United States Patent [19]

Wong et al.

[11] Patent Number: 5,003,826
[45] Date of Patent: Apr. 2, 1991

[54] APPARATUS FOR SUPPORTING A LONG CABLE FOR TENSION TESTING

[75] Inventors: Kin Y. Wong, Renton; Douglas Thompson, Redmond, both of Wash.

[73] Assignee: The Boeing Company, Seattle, Wash.

[21] Appl. No.: 491,761

[22] Filed: Mar. 12, 1990

[51] Int. Cl.⁵ .............................................. G01N 3/08
[52] U.S. Cl. .................... 73/828; 24/115 R
[58] Field of Search ............... 73/828, 830, 158; 24/115 R, 115 K, 115 M; 188/65.1

[56] References Cited

U.S. PATENT DOCUMENTS

| | | | |
|---|---|---|---|
| 357,715 | 2/1887 | Kent | 73/829 |
| 1,453,027 | 4/1923 | Tham et al. | 24/115 R X |
| 2,291,086 | 7/1942 | Lessig | 73/829 |
| 2,435,266 | 2/1948 | Brillhart | 73/826 |
| 2,584,282 | 2/1952 | Nelson. | |
| 3,171,277 | 3/1965 | Gloor. | |
| 3,342,067 | 9/1967 | Bush | 73/158 |
| 4,145,920 | 3/1979 | Yamagami | 73/158 |
| 4,653,331 | 3/1987 | Inouye et al. | 73/826 |

Primary Examiner—Jerry W. Myracle

[57] ABSTRACT

A device for supporting a long cable to permit the ends of the cable, such as swaged end fittings, to be tested by a conventional tension/compression tester. The device includes a drum upon which the cable is wound. The drum is supported by a pair of vertical flanges which in turn are connected to a movable platform of the tension/compression tester. One end of the cable is connected to a fixed base of the tester. A small section of the remaining portion of the cable that is not wound around the drum is engaged by a movable clamp which is fastened to one of the vertical flanges. The cable is tested by movement of the platform away from the base until a predetermined load is reached. A majority of the applied force is absorbed by the portion of the cable that is wound on the drum. The remainder of the applied force is absorbed by the adjustable clamp. Consequently, during the test there is limited slippage of the cable on the drum.

6 Claims, 2 Drawing Sheets

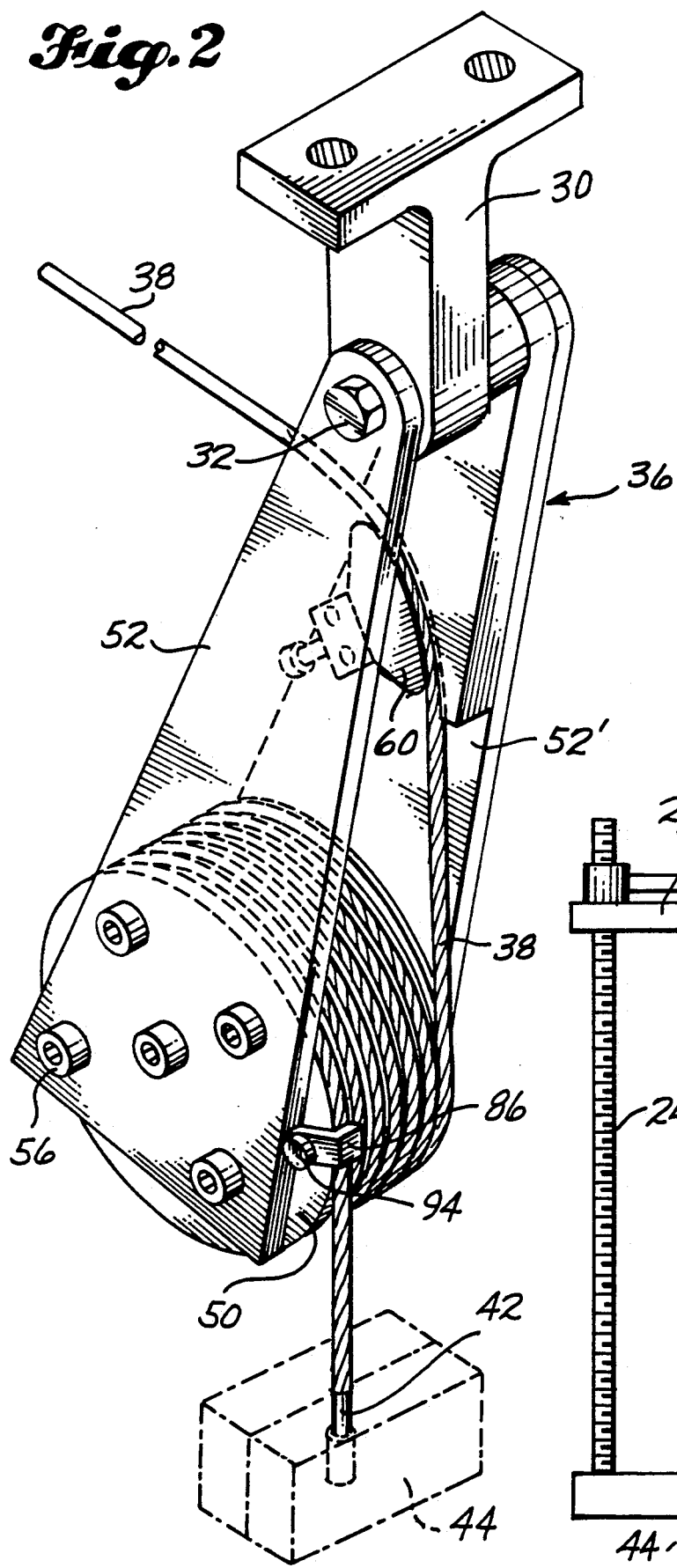
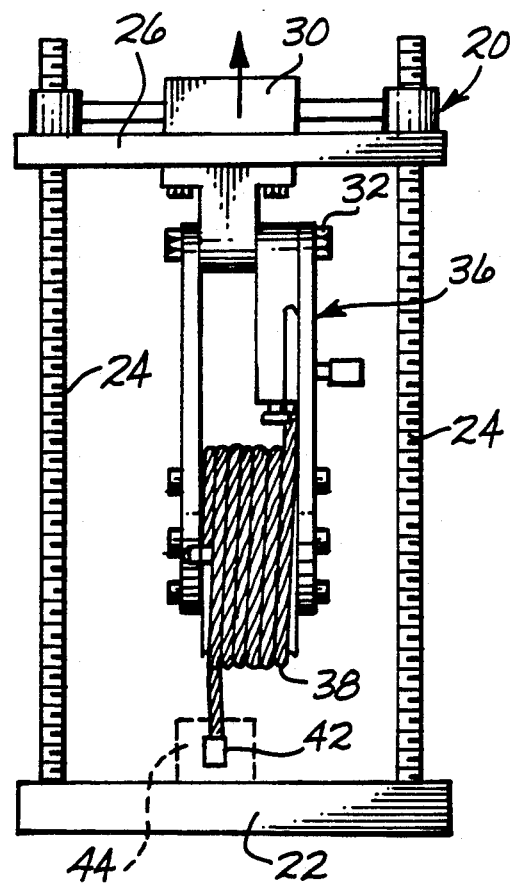

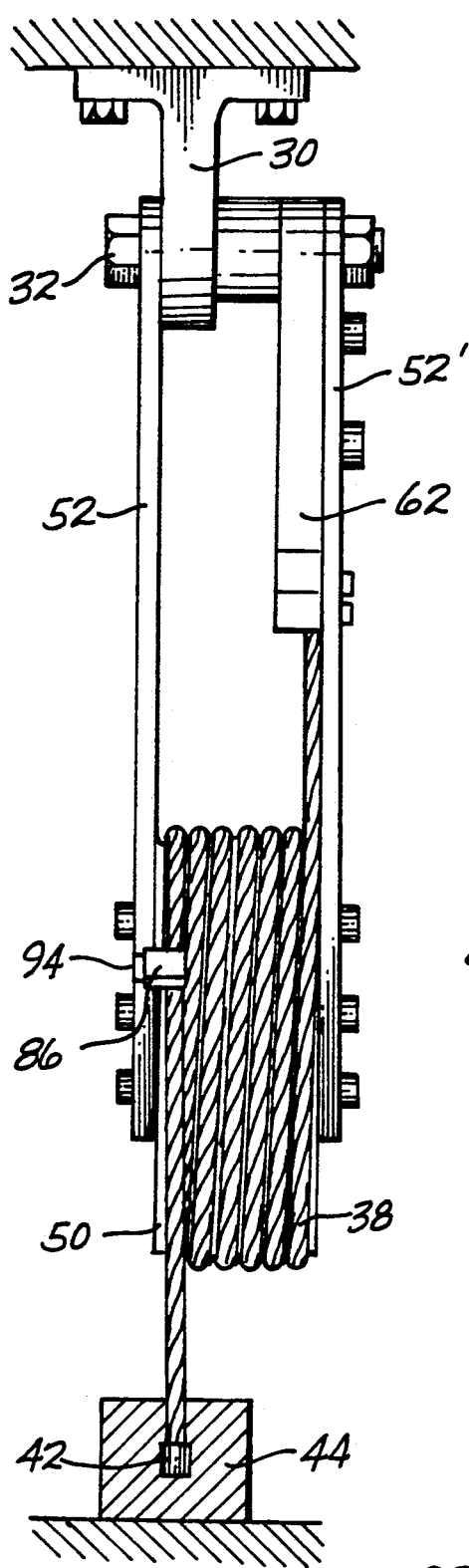
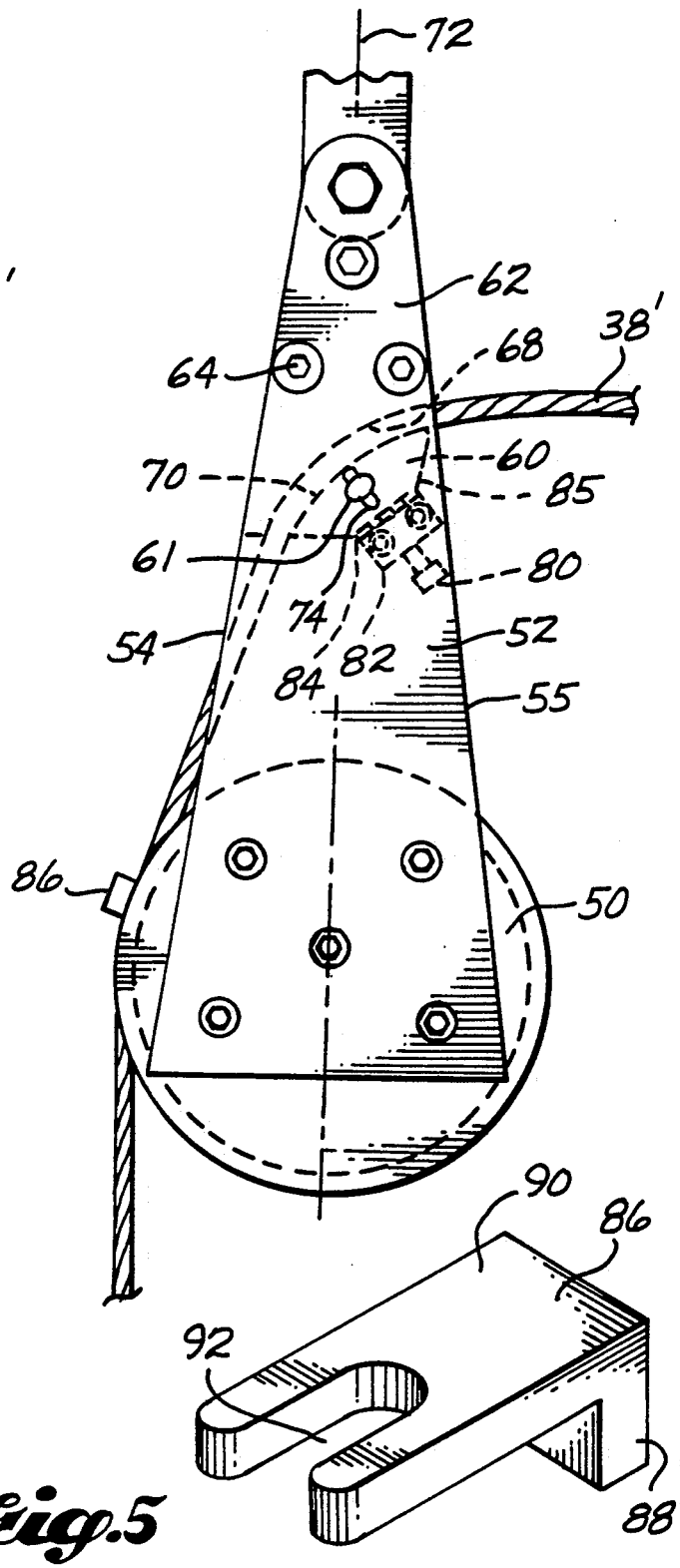

APPARATUS FOR SUPPORTING A LONG CABLE FOR TENSION TESTING

TECHNICAL FIELD

The present invention relates to a device for supporting a long cable for testing, and more particularly to a device for supporting a long cable to permit fittings swaged to the ends of the cable to be tested for strength.

BACKGROUND OF THE INVENTION

Many aircraft systems are controlled by means of wire cables. Typically these cables have fittings which are swaged to the ends of the cables and which allow the cables to be connected to the various aircraft systems. It is desirable to test these cables to ensure that the fittings are securely fastened thereon.

It is common to test cables which have lengths of approximately six feet or less on a tension/compression testing machine such as the Tinius Olsen Tester manufactured by Tinius Olsen Testing Machine Company of Willow Grove, Pa. Since the maximum travel of the Tinius Olsen Tester does not exceed about six feet, cables which exceed this length must be tested by other methods.

Many wire control cables have lengths which exceed one hundred feet. It is desirable, therefore, to be able to use a machine such as the Tinius Olsen Tester to test the end fittings on these longer cables.

Conventionally, a number of long cable testing devices have been disclosed. For example, U.S. Pat. No. 3,342,067 by Bush discloses a device for testing end fittings of a long cable wherein the device includes a drum upon which a portion of the cable is wound.

SUMMARY OF THE INVENTION

The present invention pertains to apparatus for supporting a cable in a cable testing machine. The apparatus includes a frame which is connected to the machine, and a drum which is connected to the frame and which supports the cable which is wound therearound. There are means, connected to the frame, for engaging a first portion of the cable which is not wound around the drum so as to prevent movement of the cable relative to the drum. The invention also includes means for connecting a second portion of the cable to a fastener on the cable testing machine such that the cable is tested by operation of the cable testing machine. During this operation, the cable is placed under tension by movement of the drum relative to the fastener.

BRIEF DESCRIPTION OF THE DRAWINGS

The present invention will be described in greater detail in the following Detailed Description in conjunction with the attached drawings, in which:

FIG. 1 is a front view showing the cable support tester of the present invention installed on a conventional tension/compression testing machine;

FIG. 2 is an isometric view of the cable support tester of the present invention;

FIG. 3 is an end view of the cable support tester;

FIG. 4 is a side view of the cable support tester; and

FIG. 5 is an isometric view of an adjustable clip which is installed on the cable support tester.

DETAILED DESCRIPTION

As discussed briefly in the foregoing Background of the Invention, the present invention is used in conjunction with a conventional tension/compression testing machine in order to test long cables. A typical tension/compression testing machine, such as the Tinius Olsen Tester, is indicated at 20 in FIG. 1. The tester 20 includes a fixed lower base 22 which supports a pair of vertical threaded shafts 24. Threadably mounted on the shafts 24 is an upper platform 26 which is caused to move in the vertical direction by rotation of the shafts 24. The shafts 24 are rotated by means of a motor and drive assembly not shown. Also included in the tester 20 is a T-block 30 which is bolted to the upper platform 26. At the lower end of the block 30 is a hole for received a bolt 32 therethrough.

The bolt 32 supports a unique cable support assembly indicated at 36 in FIG. 1. Briefly, a portion of the cable under test 38 is wound around the assembly 36 in a manner that a fitting 42 located at one end of the cable is inserted within a catch 44 which is fastened to the fixed base 22. Testing of the fitting 42 is initiated by upper movement of the platform 26 and the cable support assembly 36 therewith until a pre-determined tension testing limit is reached. A fitting (not shown) located at the opposite end of the cable is tested by removing the cable from the drum, placing this fitting under test in the catch 44, rewinding the cable on the drum, and then repeating the test.

Referring now to FIGS. 2 and 3, the cable support assembly 36 includes a cylindrical drum 50 which is supported at its opposite ends by a frame formed by parallel left and right triangular-shaped flanges 52, 52' respectively, each having a front edge 54 and a rear edge 55 (FIG. 4). In order to attach the cable support assembly to the tester 20, the upper narrow ends of the flanges 52, 52' include holes (not shown) for receiving the attachment bolt 32 therethrough. Furthermore, the flanges 52, 52' are secured at their lower ends to the opposite sides of drum 50 by bolts 56.

In order to engage a portion of the remaining length of cable 38 which is not wound around the drum, the assembly 36 includes an adjustable clamp 60 (FIG. 2) which is connected to the inner surface of the right flange 52' by means of an adjustable thumbscrew 61 (FIG. 4) which is installed in a manner that its shaft is perpendicular to the inner surface of the right flange 52'. The cable 38 is sandwiched between the adjustable clamp 60 and a clamp pad 62 which is fixed to the inner surface of the right flange 52' by screws 64. As shown in FIG. 4, the lower surface 68 of the clamp pad 62 has a somewhat concave shape such that the surface 68 extends in an upward and rearward direction. An upper surface 70 of the clamp 60 has a somewhat convex shape such that this surface extends in an upward and rearward direction which is complementary to the surface 68. Thus, the cable 38 is supported so that it extends from the drum 50 near the front edge 54 of the frame in an upward and rearward direction. The cable is engaged between the clamp 60 and the clamp pad 62 so that it extends further upward and rearward whereupon exiting the clamp and clamp pad, the cable is approximately perpendicular to that vertical portion of the cable suspended over the catch 44.

As shown in FIG. 4, the flange 52' includes a vertical lengthwise axis shown by a line designated by the number 72. In order to allow movement of the clamp 60 on the flange 52', the clamp 60 includes an oblong slot 74 which intersects the axis 72 at about a forty five degree angle such that the slot 74 extends from a location near the upper surface 70 in a downward and rightward direction (when viewing FIG. 4). This allows the clamp 60 (i) to be rotated about the shaft of the thumbscrew 61 and (ii) to be moved away from the clamp pad 62 when inserting the cable 38, and then moved back into position wherein cable is sandwiched between the clamp 60 and the clamp pad 62.

In this manner, there are no sharp bends in the cable 38. More specifically, by locating the clamp 60 at a forty five degree angle and providing a curved clamping surface, any sharp bends in the cable are avoided. For example, if the surface 70 of the clamp were located in a generally horizontal manner, the cable would have a sharp bend at a location adjacent to the left edge of the clamp (when viewing FIG. 4). On the other hand, if the surface 70 of the clamp were located in a generally vertical manner, the clamp 60 would have a sharp bend at a location adjacent to the right edge of the clamp due to the tendency of the free end 38' of the cable to bend downward toward the ground.

Further support for the clamp 60 is provided by an adjustment screw 80 (FIG. 4) which is threaded inside a rectangular support block 82 which in turn is fastened to the inner surface of the flange 52'. The end of the adjustment screw 80 is located parallel to the inner surface of the flange 52' and it extends beyond a front flat surface 85 of the block 82 where it engages a rear flat surface 84 of the adjustable clamp 60. In this manner, the pressure applied to the cable 38 by the clamp 60 is adjustable by operation of the adjustment screw 80. In the present invention, the front surface 85 of the support block 82 is positioned near the rear surface 84 of the clamp so that pivotal movement of the clamp is limited by engagment of the clamp rear surface 84 with the block front surface 85. This places the clamp in the approximate desired position for engaging the cable.

More specifically, prior to moving the clamp 60 into position against the cable, the position of the clamp 60 about the thumbscrew 61 is dictated by the engagement of the rear surface of the clamp 60 with the front surface 85 of the support block 82. However, when the clamp 60 is moved away from the support block 82 and is tightened against the cable 38 by operation of the adjusting screw 80, the clamp is free to pivot slightly about the thumscrew and therefore is automatically aligned with the cable. This results in a uniform pressure along the length of the cable and therefore the cable is not damaged.

The cable 38 also is engaged by an L-shaped clip 86 (FIG. 5) having a short end 88 which is joined to a perpendicular longer side 90. The longer side 90 includes a U-shaped notch 92 which is engaged by a screw 94 (FIG. 2) on the drum 50. The clip 86 is fastened to the drum 50 such that the short end 88 of the clip extends over the edge of the drum and engages a portion of the cable 38 which extends down to the catch 44.

In the present invention, the majority of the applied force generated by the tester 20 is absorbed by the friction of the cable 38 around the drum 50. The remainder of the applied force is absorbed by the clamp 60 and clamp pad 62. Furthermore, to ensure that the cable 38 remains tightly wound around the drum 50 and thereby ensure there is sufficient friction between the cable and the drum, the clip 86 lightly engages the cable 38 in an interference fit. The slot 92 permits the clip 86 to be installed over the cable after it is wound around the drum. In this manner, there is limited movement of the cable as a result of the force applied to the cable by upward movement of the tester platform.

In the present embodiment, the surface of the drum includes grooves (not shown) for holding six complete turns of cable. The size of the grooves are dependent on the diameter of the cable to be tested.

What is claimed is:

1. Apparatus for supporting a cable having a first end which is attachable to a cable testing machine and a second end, the apparatus comprising:
   a. a frame which is connected to the cable testing machine so as to support the frame in a vertical manner;
   b. a drum which is connected to the second end of the frame and which supports a portion of the cable which is wound around the drum; and
   c. means, connected to the frame at a location above the drum, for engaging a portion of the cable which is not wound around the drum so as to prevent movement of the wound portion of the cable relative to the drum when the cable testing machine causes the drum to move relative to the first end of the cable in a vertical direction in order to place the first end of the cable under tension, the cable engaging means including a clamp pad which is fixedly connected to the frame and which has a first curved surface, and a clamp which has a second curved surface having a shape that is complementary to the first surface and which is movably connected to the frame so as to engage the cable between the first and second surfaces in a manner that the cable extends from the drum in an upward direction where it is caused to curve between the first and second surfaces so that the cable exits from the cable engaging means in a generally horizontal manner so as to minimize any bending of the cable, the engaging means being connected to the frame in a manner that the cable extends from the drum at a location near a front edge of the frame in a direction toward a rear edge of the frame such that the portion of the cable engaged by the engaging means continues to extend upward and toward the rear edge of the frame.

2. The apparatus as set forth in claim 1 wherein:
   a. the engaging means includes means for connecting the movable clamp to the frame in a manner to allow the clamp to move in a first direction toward the clamp pad and in a second direction away from the clamp pad; and
   b. the engaging means includes means for moving the clamp in the first direction, the moving means including (i) screw means and (ii) means for supporting the screw means on the frame such that rotation of the screw means causes the clamp to move in the first direction so as to engage the cable.

3. The apparatus as set forth in claim 2, wherein:
   a. the engaging means engages the cable in a first plane;
   b. the engaging means further includes means for connecting the movable clamp to the frame so as to allow the movable clamp to pivot about a pivot axis which is perpendicular to the first plane such that when the movable clamp is caused to move in the first direction against the cable, the movable clamp pivots about the pivot axis so as to align with the cable.

4. The apparatus as set forth in claim 3 wherein the screw support means is connected to the frame such that the screw support means is positioned relative to the clamp so as to limit the amount of pivotal movement of the clamp about the pivot axis so that the clamp curved surface remains generally aligned, with the clamp pad curved surface.

5. The apparatus as set forth in claim 4 wherein:
   a. the movable clamp includes a rear surface;
   b. the screw support means includes a front surface; and
   c. the screw support means is connected to the frame such that amount of movement of the clamp about the pivot axis is limited by engagement of the clamp rear surface with the front surface of the screw support means.

6. Apparatus for supporting a cable having a first end which is attachable to a cable testing machine and a second end, the apparatus comprising:
   a. a frame which is connected to the cable testing machine so as to support the frame;
   b. a drum which is connected to the second end of the frame and which supports a portion of the cable which is wound around the drum; and
   c. means, connected to the frame, for engaging a portion of the cable which is not wound around the drum so as to prevent movement of the wound portion of the cable relative to the drum when the cable testing machine causes the drum to move relative to the first end of the cable in order to place the first end of the cable under tension, the cable engaging means including a clamp pad which is fixedly connected to the frame and which has a first curved surface, and a clamp which has a second curved surface having a shape that is complementary to the first surface and which is movably connected to the frame so as to engage the cable between the first and second surfaces in a manner that the cable extends from the drum where it is caused to curve between the first and second surfaces so that the cable exits from the cable engaging means so as to minimize any bending of the cable, the engaging means being connected to the frame in a manner that the cable extends from the drum at a location near a front part of the frame in a direction toward a rear part of the frame such that the portion of the cable engaged by the engaging means continues to extend toward the rear part of the frame.

* * * * *